United States Patent

Griswold

[11] Patent Number: 5,947,960
[45] Date of Patent: Sep. 7, 1999

[54] VENTING CRYOSURGICAL INSTRUMENT

[75] Inventor: Thomas A. Griswold, Ellington, Conn.

[73] Assignee: Brymill Corporation, Vernon, Conn.

[21] Appl. No.: 09/032,471

[22] Filed: Feb. 26, 1998

[51] Int. Cl.⁶ .................................................. A61B 17/36
[52] U.S. Cl. ............................................. 606/22; 62/293
[58] Field of Search ................................ 606/20, 22, 25, 606/26; 607/104, 114; 62/48.1, 293

[56] References Cited

U.S. PATENT DOCUMENTS 3,425,417  2/1969  Kanbar et al. ............................. 606/25
4,116,199  9/1978  Byrne ......................................... 606/22

Primary Examiner—Lee Cohen
Attorney, Agent, or Firm—M. P. Williams

[57] ABSTRACT

The cap which is threaded onto the dewar of a cryosurgical instrument has a vent hole therethrough which is normally closed off by a gasket when the cap is secured to the dewar, but which can allow the venting of gaseous cryogen therethrough when the cap is loosened. The threads of the cap have a scalloped region in which the threads have been machined away so as to provide a passage for gaseous cryogen, whereby, when the cap is loosened on the dewar, pressure therein is released by gas escaping either through the hole or through the scalloped region of the threads.

3 Claims, 3 Drawing Sheets

VENTING CRYOSURGICAL INSTRUMENT

RELATED INVENTIONS

The subject matter herein relates to commonly owned, copending U.S. patent applications filed contemporaneously herewith entitled "Cryosurgical Instrument", Serial No. D-(Docket No. B-44) and entitled "Fail-Safe Cryosurgical Instrument", Serial No. (Docket No. B-46).

TECHNICAL FIELD

This invention relates to relieving the pressure within the dewar of a cryosurgical instrument as the dewar cap is loosened.

BACKGROUND ART

A cryosurgical instrument disclosed in U.S. Pat. No. 4,269,390 employing a standard, double walled, evacuated, metal vacuum bottle or dewar, has a collar metallurgically bonded to the top of the dewar near the mouth thereof to provide machine threads for releasably engaging the delivery and control portion of the instrument, which is mounted on a cap having internal threads, to the dewar of the instrument. The cap has a valve mounted thereon which controls the flow of nitrogen from a feed tube in the dewar to a nozzle mounted on a delivery tube. The valve is opened by a valve operating lever. The cryosurgical instrument of said patent has been in service around the world, with minor modifications, since 1976.

In order to avoid explosive splashing of cryogenic liquid when the cap is removed from the dewar of such an instrument, it has been common in the past to lift the cap of a pressure relief valve, thereby allowing gaseous cryogen to escape, relieving the pressure within the dewar. With the advent of more streamlined pressure relief valves, however, the movement of the pressure relief valve to relieve pressure within the dewar became difficult, and created the risk of undesirable freezing of the skin as a consequence of cold cryogenic gas emanating from the valve. In an attempt to overcome this problem, the threads of the cap have been machined away at one point, so as to provide a passage for the escape of gas once the cap was loosened sufficiently to allow gas to pass by a gasket, such as one-quarter or one-half of a turn. However, it was found that this expedient worked sometimes, but more frequently did not work, so that the operator frequently had to revert to raising of the pressure relief valve in order to release the pressure in the dewar.

DISCLOSURE OF INVENTION

Objects of the invention include improved venting of the dewar of a cryosurgical instrument when the cap is being removed.

This invention is predicated in part on the discovery that gas pressure within the dewar acting against a gasket within the dewar cap may cause the gasket to block the passage formed by machining away a small section of threads, thereby not allowing gas to be vented to depressurize the dewar as a consequence of turning the cap.

According to the present invention, the cap of the dewar of a cryosurgical instrument has a hole therethrough which is normally blocked by the gasket when the cap is tightened on the dewar, but which can release gas when the cap is loosened sufficiently for the gasket to clear the hole, the cap also having a scallop shaped passage formed by machining away the threads of the cap in the vicinity of the aforementioned hole. The invention, by having both the passage formed in the threads and a passage formed by a hole in the cap, the two passages being within a workable distance of each other, always provides one of two paths for gas to escape. If the gasket is blocking the passage through the threads, when the cap is loose, it cannot be blocking the hole through the cap. Similarly, when the cap is loosened, if the gas pressure keeps the gasket pressed against the hole, thereby sealing it, it cannot be blocking the passage through the threads. Thus, a quarter or half turn of the cap will always result in depressurizing the dewar, in every case.

Other objects, features and advantages of the present invention will become more apparent in the light of the following detailed description of exemplary embodiments thereof, as illustrated in the accompanying drawing.

BEST MODE FOR CARRYING OUT THE INVENTION

Figure 1:
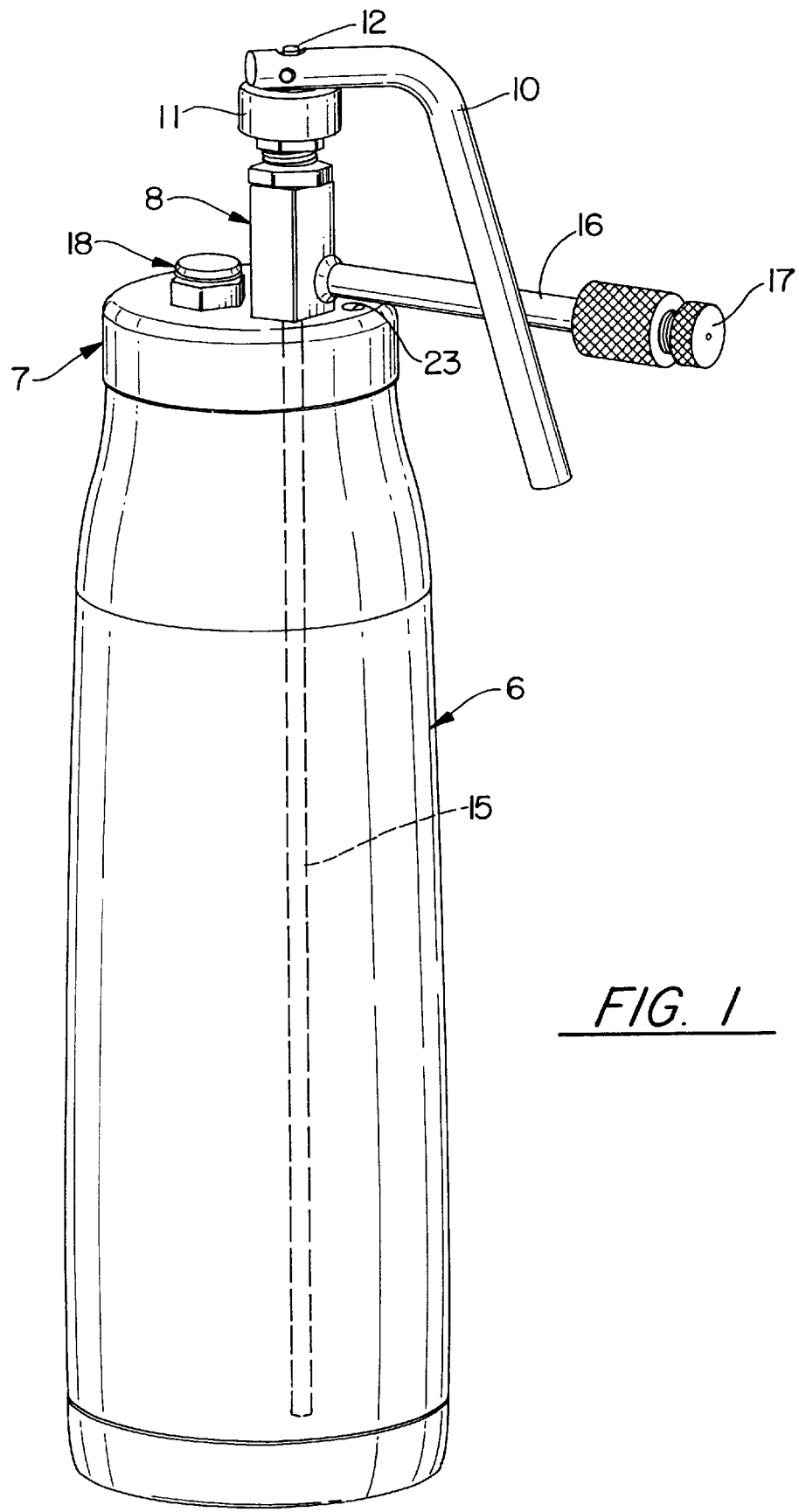
FIG. 1 is a perspective view of a cryosurgical instrument incorporating the present invention.

Referring to FIG. 1, a cryosurgical instrument in which the present invention may be practiced includes a dewar 6, at the opening of which are threads to receive a threaded cap 7 which comprises the delivery and control portion of the instrument. The cap 7 has a main valve 8 disposed thereon, the valve having a valve operating lever 10 working with a fulcrum 11 to raise a stem 12 of a valve so as to regulate the flow of cryogenic fluid from within the dewar 6 along a feed tube 15 into a delivery tube 16 to a nozzle 17. The fluid pressure within the dewar 6 is maintained by a pressure relief valve 18. The functions, although not the appearance, of the instrument as thus far described are similar to those in said patent.

Figure 4:
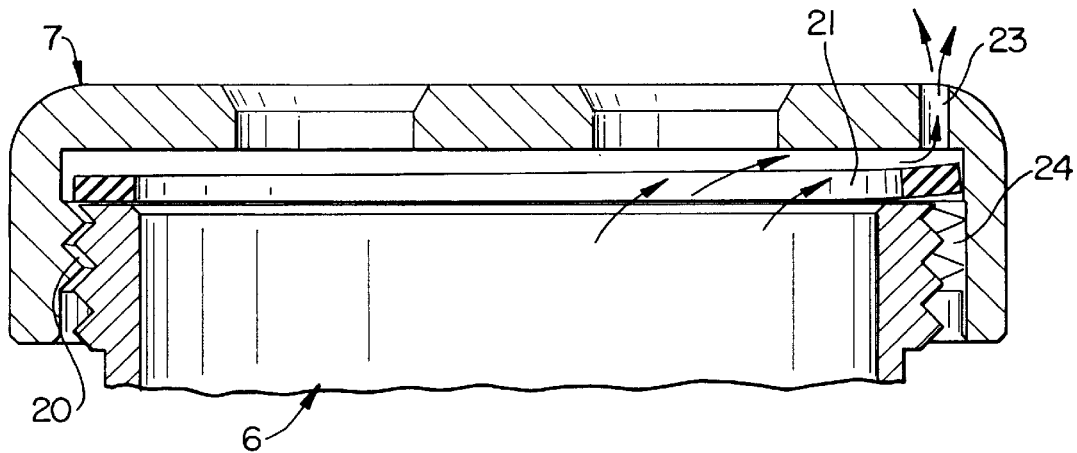
FIG. 4 is a partial sectioned side elevation view taken on the line X—X in FIG. 2, and the top of the dewar, with a gasket blocking the venting of gaseous cryogen through the passage in the threads of the cap while passing the gaseous cryogen through a hole.
Figure 5:
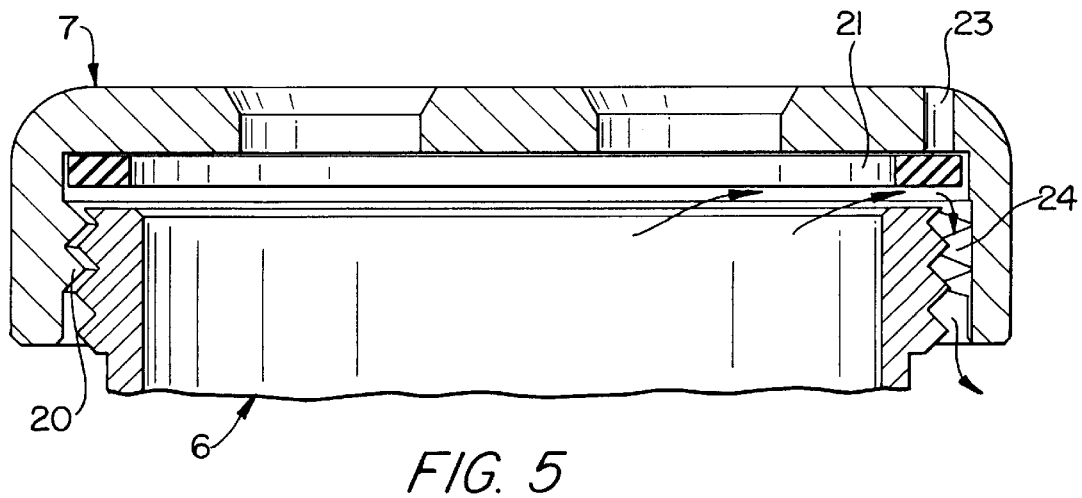
FIG. 5 is a partial, sectioned side elevation view taken on the line X—X of FIG. 2, and the top of the dewar, with a gasket blocking the venting of gaseous cryogen through a hole, but allowing the gaseous cryogen to flow through a passage in the threads of the cap.

Referring to FIGS. 2–5, the cap 7 has internal threads 20 which capture a gasket 21 which usually overlies a hole 23, thereby blocking the hole when the cap 7 is screwed tightly to the dewar 6. The threads 20 have a scallop portion 24, in which the threads have been machined away, so as to provide a passage for gaseous cryogen down through the cap, when the cap 7 is loosened on the dewar 6, and the gasket 21 is being held up against the hole 23 by gaseous pressure, as shown in FIG. 5. On the other hand, should the gasket fall downwardly, when the cap is loosened on the dewar, the gaseous cryogen can flow past the gasket and out the hole 23, as shown in FIG. 4.

Figure 2:
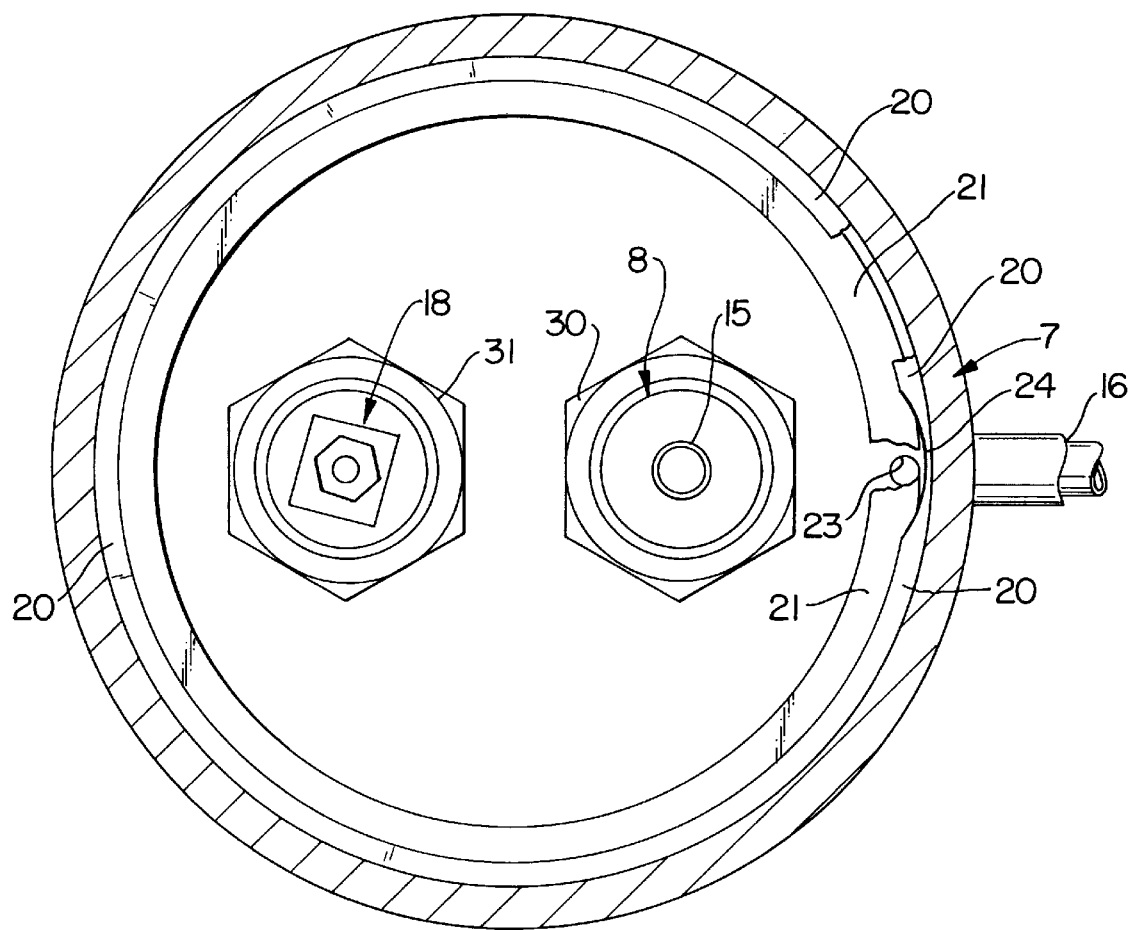
FIG. 2 is a partial, partially sectioned, partially broken away bottom plan view of the cap of the cryosurgical instrument of FIG. 1.
Figure 3:
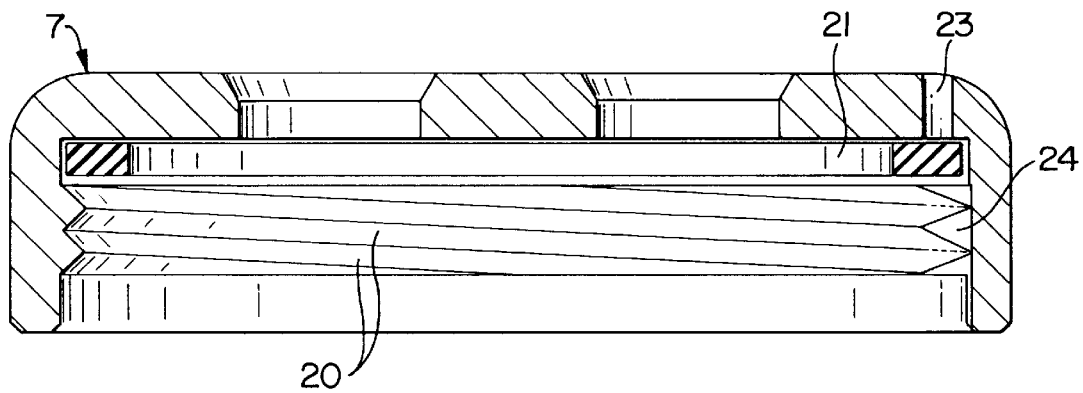
FIG. 3 is a sectioned side elevation view taken on the line X—X in FIG. 2.

The main valve 8 and pressure relief valve 18 in this embodiment, are held to the cap 7 by means of corresponding nuts 30, 31, as seen in FIG. 2. However, the invention may be practiced with valves secured to the cap in other ways.

As is seen in FIGS. 2–5, the scallop area 24 should be rather close to the hole 23 so that if the hole is blocked, the scallop axiomatically will not be blocked, and vice versa, as illustrated by comparing FIGS. 4 and 5. On the other hand, it is not necessary that the scalloped area 24 be perfectly aligned with the hole 23, as shown. In the embodiment herein, the hole 23 is positioned directly beneath the feed tube 16. This is to cause any gas which emanates through the hole 23 to be dispersed, thereby providing the least risk to the operator. However, the invention may be practiced with the hole in a different position relative to the feed tube 16 or other components on the cap 7.

In the present embodiment, the hole 23 is drilled through the top surface of the cap. However, the invention may as readily be practiced with the hole located in the rim of the cap, provided such hole can vent the cryogen (in a manner obvious when viewing FIG. 4). As seen in FIG. 2, the scalloped area 24 does not, in this embodiment, completely obliterate the threads in the vicinity of the hole 23. However, it may be preferable to have the scalloped area 24 deeper, thereby totally eliminating the threads in that region, and possibly even cutting into the rim of the cap.

Thus, although the invention has been shown and described with respect to exemplary embodiments thereof, it should be understood by those skilled in the art that the foregoing and various other changes, omissions and additions may be made therein and thereto, without departing from the spirit and scope of the invention.

I claim:

1. A cryosurgical instrument comprising:

a dewar for containing liquid cryogen, the mouth of said dewar having threads;

a cap having threads complementary to the threads on said dewar, said cap having a delivery and control portion of the cryosurgical instrument disposed thereon; and a gasket within said cap;

wherein the improvement comprises:

a vent hole positioned in said cap over said gasket; and a scalloped region in the vicinity of said vent hole, said scalloped region consisting of an area of said cap where said threads have been machined away to provide a passageway for gaseous cryogen, whereby, when the cap is loosened on the dewar, gaseous cryogen may escape around the gasket either through said hole or through said scalloped region, thereby releasing the pressure in said dewar.

2. The instrument according to claim 1 wherein the center of said scalloped region and the center of said hole are disposed substantially on the same major axis of said cap.

3. An instrument according to claim 1 wherein said hole is disposed in a top surface of said cap immediately above said scalloped area.

* * * * *